(12) United States Patent
Bonnet et al.

(10) Patent No.: US 7,253,312 B2
(45) Date of Patent: Aug. 7, 2007

(54) PROCESS FOR PRODUCING CARBOXYLIC ACIDS

(75) Inventors: Didier Bonnet, Lyons (FR); Tania Ireland, Lyons (FR); Jean-Pierre Simonato, Sassenage (FR)

(73) Assignee: Rhodia Polyamides Intermediates, Saint_Fons (FR)

( * ) Notice: Subject to any disclaimer, the term of this patent is extended or adjusted under 35 U.S.C. 154(b) by 133 days.

(21) Appl. No.: 10/533,212

(22) PCT Filed: Oct. 8, 2003

(86) PCT No.: PCT/FR03/03198

§ 371 (c)(1),
(2), (4) Date: Apr. 28, 2005

(87) PCT Pub. No.: WO2004/041765

PCT Pub. Date: May 21, 2004

(65) Prior Publication Data

US 2006/0106251 A1    May 18, 2006

(30) Foreign Application Priority Data

Oct. 30, 2002 (FR) .................................. 02 13576

(51) Int. Cl.
*C07C 55/00* (2006.01)
*C07C 51/31* (2006.01)
*C07C 51/42* (2006.01)

(52) U.S. Cl. ........................ 562/590; 562/543; 562/593

(58) Field of Classification Search ................ 562/543, 562/590, 593
See application file for complete search history.

(56) References Cited

U.S. PATENT DOCUMENTS 6,433,220 B1 *  8/2002  Dudgeon et al. ........... 562/543
6,787,669 B1 *  9/2004  Costantini et al. .......... 562/543

\* cited by examiner

*Primary Examiner*—J. Parsa

(57) ABSTRACT

The present invention relates to a process for producing carboxylic acids. It relates more particularly to a process for producing carboxylic acids by oxidation of a hydrocarbon with oxygen or a gas containing oxygen, and even more particularly to the oxidation of cyclohexane to adipic acid. It relates to a process comprising a step consisting of hydrolysis of the esters formed during the oxidation step.

21 Claims, No Drawings

PROCESS FOR PRODUCING CARBOXYLIC ACIDS

This application is an application under 35 U.S.C. Section 371 of International Application Number PCT/FR03/03198 filed on Oct. 28, 2003.

The present invention relates to a process for producing carboxylic acids.

It relates more particularly to a process for producing carboxylic acids by oxidation of a hydrocarbon with oxygen or a gas containing oxygen, and even more particularly to the oxidation of cyclohexane to adipic acid.

Adipic acid is an important chemical compound used in many fields. Thus, adipic acid can be used as an additive in many products, both in the area of foods and in concrete. However, one of the most important uses is its application as a monomer in the production of polymers, including polyurethanes and polyamides.

Several processes for producing adipic acid have been proposed. One of the most important, used industrially on a large scale, consists in oxidizing, in one or two step(s), cyclohexane to a mixture of cyclohexanol/cyclohexanone with a gas containing oxygen or with oxygen. After extraction and purification of the cyclohexanol/cyclohexanone mixture, these compounds are oxidized in particular to adipic acid with nitric acid.

However, this process has a major drawback associated with the formation of nitrous vapour.

Many studies have been carried out in order to develop a process for oxidizing hydrocarbons with oxygen or a gas containing oxygen, that makes it possible to directly obtain carboxylic acids, mainly adipic acid.

These processes are described in particular in patents FR 2,761,984, FR 2,791,667, FR 2,765,930 and U.S. Pat. No. 5,294,739.

Generally, the reaction is carried out in a solvent medium, the solvent being a monocarboxylic acid such as acetic acid. Other solvents have been proposed, for instance the carboxylic acids that are lipophilic in nature, described in Patent FR 2,806,079.

Many patents have described the operating conditions for this reaction and also the various steps for extracting the acids formed, purifying them and also recycling the non-oxidized hydrocarbon and the catalyst.

However, in this oxidation reaction, by-products form that can more or less substantially decrease the yield of the process. Among these, by-products containing an alcohol function, such as cyclohexanol, are particularly harmful. In fact, they can react with the acids formed, so as to give esters and thus to greatly decrease the yield of recovered carboxylic acids. According to the method of extraction and of separation of the acids, the esters are either recycled with the non-oxidized hydrocarbon or are entrained with the recovered acids. The presence of esters in the reaction medium can result in a decrease in the activity of the catalyst and especially in the formation of unwanted by-products resulting from the oxidation of these esters.

The problem of ester formation is all the more substantial since the oxidation reaction is less selective for acids.

One of the aims of the present invention is to propose a process for producing carboxylic acids by oxidation of hydrocarbons using oxygen or a gas containing oxygen, in which the harmful effect of the esters formed is decreased.

To this effect, the invention proposes a process for producing carboxylic acids by oxidation of a hydrocarbon with oxygen or a gas containing oxygen, in the presence of a monocarboxylic acid-based solvent and of an oxidation catalyst, characterized in that the reaction medium is treated so as to separate and extract the carboxylic acids formed during the oxidation, and in that hydrolysis of the esters formed during the oxidation reaction is carried out by treatment of the reaction medium, either before separation of said acids formed, or after separation of said acids formed by treatment of the organic phase derived from the reaction medium.

According to a preferential characteristic of the invention, the hydrolysis is carried out by addition to the medium to be treated of a strong acid and maintenance of said medium at a temperature of greater than 50° C., preferably of between 80° C. and 200° C.

The period of time for which the temperature is maintained depends on the amount of esters to be hydrolysed, and is determined in a usual manner by those skilled in the art during the setting of the operating parameters of the process.

In order to perform the hydrolysis, water can be added to the medium to be treated. However, this addition of water can be eliminated if the amount present in the medium or the water added with the strong acid is sufficient.

As strong acid that is suitable for the invention, acids having a pKa of less than 2 are preferred. By way of example, mention may be made of sulphonic acid, sulphuric acid, nitric acid, hydrochloric acid, hydrobromic acid, orthophosphoric acid, triflic acid, or the like.

Generally, the amount of strong acid added is defined so as to have a concentration by weight of less than approximately 10% relative to the weight of the reaction medium, preferably of between 0.1 and 10%, advantageously of between 0.1 and 4%.

In one embodiment of the invention, the strong acid is added in pure form, preferably in the form of a concentrated solution.

According to another embodiment of the invention, the strong acid is added in a form that is carried on or attached to an inert material such as a resin. This embodiment makes it possible to carry out the hydrolysis under ideal conditions and to be able to readily separate and recover the strong acid. As acid compounds that are suitable for the invention, mention may be made, by way of example, of sulphonic resins. However, any other equivalent resin or carrier for strong acid functions may be used, since the invention is not limited to the use of sulphonic resins.

In one embodiment of the invention, the extraction or separation, from the reaction medium, of the carboxylic acids formed is carried out by means of separation by settling out of the reaction medium into two phases, an aqueous phase and an organic phase. This separation by settling out is obtained or promoted directly by cooling of the reaction medium, when the concentration of water present in said medium is sufficient to obtain the formation of two phases. When the amount of water present is not sufficient, an additional amount of water is added to the reaction medium before carrying out the separation by settling out, before or after cooling.

In another embodiment of the invention, the extraction of the carboxylic acids formed can be carried out by means of a liquid/liquid extraction by treatment of the reaction medium derived from the reactor with an extraction liquid.

The monocarboxylic acid solvent present in the reaction medium is advantageously insoluble in the extraction liquid.

For the purpose of the patent, the products are considered to be insoluble in the extraction liquid if their solubility in said liquid, measured at 90° C. and under atmospheric pressure, is less than or equal to 10% by weight relative to the liquid.

According to the invention, the hydrolysis of the esters is advantageously carried out in the medium obtained after extraction of the carboxylic acids according to one of the embodiments described above, or by filtration if the carboxylic acid produced crystallizes after cooling of the reaction medium.

However, the hydrolysis of the esters can, according to the invention, also be carried out in the reaction medium before the extraction or the separation of the carboxylic acids formed. In this embodiment, the acids will be extracted or recovered from the medium according to the techniques described above, after the hydrolysis of the esters has been carried out.

According to a preferred embodiment of the invention, the treatment with a strong acid is advantageously carried out after elimination, by evaporation or distillation, of the organic compounds exhibiting a boiling point of less than or equal to that of the alcohols and/or ketones formed during the oxidation reaction. Thus, in the case of the oxidation of cyclohexane, the cyclohexane that has not reacted, and all the organic compounds formed that have a boiling point less than that of the alcohol and of the ketone (cyclohexanol or cyclohexanone in the case of the oxidation of cyclohexane), are separated from the medium by distillation and, preferably, recycled in the oxidation step. The alcohol and the ketone (cyclohexanol and cyclohexanone) are also separated and recycled during this step. However, the treatment with a strong acid can also be carried out on the reaction medium before the separation by distillation of the organic compounds described above.

According to another embodiment of the invention, the treatment with a strong acid in order to hydrolyse the esters is carried out after elimination by distillation of the organic compounds exhibiting a boiling point less than or equal to that of the monocarboxylic solvent used to carry out the oxidation, for instance aromatic carboxylic acids. This embodiment makes it possible to recycle the acid solvent with the hydrocarbon and the ketone and alcohol compounds in the oxidation step, before any bringing into contact with a strong acid.

According to another characteristic of the invention, the reaction medium after hydrolysis of the esters is treated so as to, firstly, separate the alcohols formed and, secondly, recover the acids formed and, optionally, the monocarboxylic solvent. The separation of the alcohols formed, such as cyclohexanol in the case of the oxidation of cyclohexane, is advantageously obtained by distillation. The monocarboxylic solvent is recycled after separation of the acids formed during the hydrolysis. This separation is advantageously obtained by extraction of said acids formed, with a solvent, such as water. It is carried out either by addition of the extraction solvent and separation of the aqueous and organic phases by means of separation by settling out, or in a liquid/liquid extraction process and device, the oxidation solvent forming the organic phase.

The alcohol (cyclohexanol) separated is advantageously recycled at the oxidation step. The medium obtained after separation of the alcohols can be treated so as to recover the carboxylic acids present, by precipitation, crystallization or any other method.

Advantageously, the oxidation solvent present in the medium obtained after separation of the alcohol is separated from the dicarboxylic acids or from the aqueous phase present by, in particular, the techniques described above. The oxidation solvent thus separated is recycled in the oxidation step after, advantageously, a purification, for example by distillation. The aqueous phase containing the acids formed during the hydrolysis is, after extraction or separation of the oxidation solvent, advantageously mixed with the aqueous phase containing the diacids formed during the oxidation, extracted on leaving the oxidation step, or obtained in the step of extraction of these diacids, or treated directly so as to recover the acids present. This aqueous phase containing the diacids formed during the hydrolysis can also be mixed with the oxidation medium leaving the oxidation step before the extraction of the diacids formed.

The medium obtained after separation of the alcohols can also be introduced into the step for liquid/liquid extraction of the carboxylic acids formed, in particular when the strong acid used to carry out the hydrolysis is in a carried form, and therefore can be readily separated from the medium before it is introduced into the liquid/liquid extraction step.

In a particular embodiment of the invention, when the strong acid is nitric acid, the alcohol formed by the hydrolysis of the esters is oxidized to an acid in the hydrolysis medium. For this, an oxidation catalyst can be added to the hydrolysis medium and the amount of strong acid added may be greater than 10% by weight. The medium obtained containing acids is added directly in the step consisting of crystallization of the dicarboxylic acid, without any step of separation and recovery of the alcohol.

The reaction medium is generally obtained from the oxidation, with oxygen or a gas containing oxygen, of a hydrocarbon, more particularly of an arylaliphatic cycloaliphatic hydrocarbon such as cyclohexane or cyclododecane. The oxidation reaction is generally carried out in the presence of a solvent. The solvent may be very varied in nature insofar as it is not substantially oxidizable under the reaction conditions. It may in particular be chosen from polarprotic solvents and polarprotic solvents. As polarprotic solvents, mention may be made, for example, of carboxylic acids having only primary or secondary hydrogen atoms, in particular aliphatic acids having from 2 to 9 carbon atoms, such as acetic acid, perfluoroalkylcarboxylic acids such as trifluoroacetic acid, alcohols such as tert-butanol, halogenated hydrocarbons such as dichloromethane, and ketones such as acetone. As polarprotic solvents, mention may be made, for example, of lower alkyl (=alkyl radical having from 1 to 4 carbon atoms) esters of carboxylic acids, in particular aliphatic carboxylic acids having from 2 to 9 carbon atoms or perfluoroalkylcarboxylic acids, tetramethylenesulphone (or sulpholane) or acetonitrile, benzonitrile.

The solvent may also be chosen from carboxylic acids that are lipophilic in nature.

The expression "lipophilic acid compound that is suitable for the invention" is intended to mean aromatic, aliphatic, arylaliphatic or alkylaromatic compounds comprising at least 6 carbon atoms, that may comprise several acid functions and that have low water-solubility, i.e. a solubility of less than 10% by weight at ambient temperature (10° C.-30° C.).

As lipophilic organic compounds, mention may be made, for example, of hexanoic acid, heptanoic acid, octanoic acid, 2-ethylhexanoic acid, nonanoic acid, decanoic acid, undecanoic acid, dodecanoic acid, stearic acid (octadecanoic acid) and their permethylated derivatives (complete substitution of the hydrogens of the methylene groups with the methyl group), 2-octadecylsuccinic acid, 3,5-ditert-butylbenzoic acid, 4-tert-butylbenzoic acid, 4-octylbenzoic acid, tert-butyl hydrogen orthophthalate, naphthenic or anthracenic acids substituted with alkyl groups, preferably of tert-butyl type, substituted derivatives of phthalic acids, and fatty diacids such as dimer fatty acid. Mention may also be made of the acids belonging to the above families and bearing various electron-donating substituents (groups with a hetero atom of the O or N type) or electron-withdrawing substituents (halogens, sulphonimides, nitro groups, sulphonato groups, or the like).

In general, the solvent is chosen so as to advantageously obtain a homogeneous phase under the temperature and pressure conditions at which the oxidation reaction is carried out. For this, it is advantageous for the solubility of the solvent in the hydrocarbon or the reaction medium to be at least greater than 2% by weight, and for at least one homogeneous liquid phase comprising at least some of the hydrocarbons to be oxidized and some of the solvent to be formed.

Advantageously, the solvent is chosen from those with low water-solubility, i.e. that have a water-solubility of less than 10% by weight at ambient temperature (10-30° C.).

However, it is possible, without departing from the context of the invention, to use a solvent having a water-solubility that is greater than that indicated above, if the partition coefficient for this compound between the organic phase(s) of the reaction medium consisting essentially of the hydrocarbon to be oxidized, the oxidation intermediates and the nonorganic phase comprising the water formed during the oxidation reaction makes it possible to obtain a concentration of the solvent in said aqueous phase of less than 10% by weight.

The oxidation is in general carried out in the presence of a catalyst. This catalyst advantageously comprises a metal element chosen from the group comprising Cu, Ag, Au, Mg, Ca, Sr, Ba, Zn, Cd, Hg, Al, Sc, In, Tl, Y, Ga, Ti, Zr, Hf, Ge, Sn, Pb, V, Nb, Ta, Cr, Mo, W, Mn, Tc, Re, Fe, Ru, Os, Co, Rh, Ir, Ni, Pd, Pt, lanthanides such as Ce, and combinations thereof.

These catalytic elements are used either in the form of compounds that are advantageously at least partially soluble in the liquid oxidation medium under the conditions under which the oxidation reaction is carried out, or are carried by, absorbed onto or attached to an inert support such as silica or alumina, for example.

The catalyst is preferably, in particular under the conditions under which the oxidation reaction is carried out:
either soluble in the hydrocarbon to be oxidized,
or soluble in the lipophilic acid compound,
or soluble in the hydrocarbon/lipophilic acid compound mixture forming a homogeneous liquid phase under the conditions under which the reaction is carried out.

According to a preferred embodiment of the invention, the catalyst used is soluble in one of these media at ambient temperature or at the temperature for recycling of these media in a further oxidation.

The term "soluble" is intended to mean that the catalyst is at least partially soluble in the medium under consideration.

In the case of a heterogeneous catalyst, the catalytically active metal elements are supported or incorporated in or into a microporous or mesoporous mineral matrix, or in or into a polymeric matrix, or are in the form or organometallic complexes grafted onto an organic or mineral carrier. The term "incorporated" is intended to mean that the metal is an element of the carrier or that the process is carried out with complexes that are sterically trapped in porous structures under the conditions of the oxidation.

In a preferred embodiment of the invention, the homogeneous or heterogeneous catalyst consists of salts or complexes of metals of groups IVb (the group of Ti), Vb (the group of V), VIb (the group of Cr), VIIb (the group of Mn), VIII (the group of Fe or Co or Ni) and Ib (the group of Cu) and cerium, alone or as a mixture. The preferred elements are, in particular, Mn and/or Co in combination with one or more elements chosen from the group comprising Zr, Hf, Ce, Hf and Fe. The concentrations of metal in the liquid oxidation medium range between 0.00001 and 5% (wt %), preferably between 0.001% and 2%.

Moreover, the concentration of solvent in the reaction medium is advantageously determined so as to have a molar ratio of the number of molecules of solvent and the catalytic element metal number of between 0.5 and 100 000, preferably between 1 and 5000.

The concentration of solvent in the liquid oxidation medium can vary within broad limits. Thus, it can be between 1 and 99% by weight relative to the total weight of liquid medium, more advantageously it can be between 2 and 50% by weight of the liquid medium.

It is also possible, without nevertheless departing from the context of the invention, to use the solvent in combination with another compound that may in particular have the effect of improving the productivity and/or the selectivity of the reaction of oxidation to adipic acid, and in particular the solubilization of the oxygen.

As examples of such compounds, mention may in particular be made of nitriles, hydroxyimide compounds, halogenated compounds, and more advantageously fluorinated compounds. As compounds that are more particularly suitable, mention may be made of nitriles such as acetonitrile or benzonitrile, imides belonging to the family described in European Patent EP 0824962, and more particularly N-hydroxysuccinimide (NHS) or N-hydroxyphthalimide (NHPI), halogenated derivatives such as dichloromethane, and fluorinated compounds such as:
cyclic or acyclic, fluorinated or perfluorinated, aliphatic hydrocarbons,
aromatic fluorinated hydrocarbons such as perfluorotoluene, perfluoromethylcyclohexane, perfluoroheptane, perfluorooctane, perfluorononane, perfluorodecaline, perfluoromethyldecaline, α,α,α-trifluorotoluene or 1,3-bis-(trifluoromethyl)benzene,
perfluorinated or fluorinated esters such as alkyl perfluorooctanoates or alkyl perfluorononanoates,
fluorinated or perfluorinated ketones such as perfluoroacetone,
fluorinated or perfluorinated alcohols such as perfluorohexanol, perfluorooctanol, perfluorononanol, perfluorodecanol, perfluoro-tert-butanol, perfluoroisopropanol or 1,1,1,3,3,3-hexafluoro-2-propanol,
fluorinated or perfluorinated nitriles such as perfluoroacetonitrile,
fluorinated or perfluorinated acids such as trifluoromethylbenzoic acids, pentafluorobenzoic acid, perfluorohexanoic acid, perfluoroheptanoic acid, perfluorooctanoic acid, perfluorononanoic acid or perfluoroadipic acid,
fluorinated or perfluorinated halides such as perfluoroiodooctane, or perfluorobromooctane,
fluorinated or perfluorinated amines such as perfluortripropylamine, perfluorotributylamine or perfluorotripentylamine.

The invention applies more particularly to the oxidation of cycloaliphatic compounds, such as cyclohexane or cyclododecane, to the corresponding linear diacids, adipic acid or dodecanoic acid.

According to a preferred embodiment of the invention, it relates to the direct oxidation of cyclohexane to adipic acid, with a gas containing oxygen, in a liquid medium and in the presence of a manganese catalyst.

The oxidation reaction is carried out at a temperature of between 50° C. and 200° C., preferably of between 70° C. and 180° C. It can be carried out under atmospheric pressure. However, it is generally carried out under a pressure so as to maintain the components of the reaction medium in the liquid form. The pressure can be between 10 kPa (0.1 bar) and 20 000 kPa (200 bar), preferably between 100 kPa (1 bar) and 10 000 kPa (100 bar).

The oxygen used may be in pure form or as a mixture with an inert gas such as nitrogen or helium. Air more or less enriched with oxygen may also be used. The amount of oxygen supplied to the medium is advantageously between 1 and 1000 mol per mole of compounds to be oxidized.

The oxidation process can be carried out continuously or according to a batch process. Advantageously, the liquid reaction medium that has left the reactor is treated according to known processes for, firstly, separating and recovering the diacid produced and, secondly, recycling the non-oxidized or partially oxidized organic compounds such as cyclohexane, cyclohexanol and/or cyclohexanone, the catalyst and the acid compound.

It is advantageous to also use a compound that initiates the oxidation reaction, for instance a ketone, an alcohol, an aldehyde or a hydroperoxide. Cyclohexanone, cyclohexanol and cyclohexyl hydroperoxide, which are reaction intermediates in the case of the oxidation of cyclohexane, are all particularly indicated. In general, the initiator represents from 0.01% to 20% by weight of the weight of the reaction mixture used, without these proportions having a critical value. The initiator is especially useful during the initiation of the oxidation. It can be introduced from the beginning of the reaction.

The oxidation can also be carried out in the presence of water introduced from the initial stage of the process.

As indicated above, the reaction mixture derived from the oxidation is subjected to various operations consisting in separating some of its constituents so as, for example, to allow the recycling thereof at the level of the oxidation and the recovery of the acids produced.

According to a first variant of the process, it is possible, first of all, to subject the crude reaction mixture to cooling to a temperature of 16° C. to 30° C., for example, which brings about the crystallization of at least some of the acid formed. A medium is thus obtained, comprising a solid phase consisting essentially of acid, at least one organic liquid phase containing essentially the compound to be oxidized that is not reacted, possibly the acid compound and the oxidation intermediates (or several organic phases if the acid compound and the hydrocarbon are not completely miscible at low temperature) and an aqueous liquid phase containing essentially acid by-products of the oxidation and the water formed. The catalyst may be in one of the organic phases if it is soluble in said phase, or in the lower aqueous phase.

After filtration or centrifugation of the solid, the organic and aqueous liquid phases constituting the filtrate or the centrifugate are separated, if necessary, by settling out: the organic phase(s) may be recycled in a further oxidation reaction.

It may be advantageous, prior to the operation consisting of crystallization of the acid, to concentrate the reaction mixture.

According to a second variant of the process, the final crude reaction mixture can be withdrawn under hot conditions. The reaction mixture then separates by settling out into at least two liquid phases: one or more organic phases containing essentially the hydrocarbon that has not reacted, the acid compound and the oxidation intermediates and an aqueous liquid phase containing essentially the acids formed and the water that has formed and/or been added. According to the solubility and the nature of the catalyst, it may be present in the organic phase(s), recovered by solid/liquid separation before precipitation or crystallization of the acid formed, in the case of a heterogeneous catalyst, or, if it is soluble in the aqueous phase, extracted by liquid/liquid extraction, on resin, or electrodialysis.

As in the first variant, the liquid phases are separated by settling out: the organic phase(s) can be recycled in a further oxidation reaction.

According to a third variant of the process of the invention, the reaction medium withdrawn from the reactor under hot conditions or after cooling is introduced into a step consisting of liquid/liquid extraction of the carboxylic acids formed. The extraction liquid is generally the water in which the acids formed are soluble; the organic compounds, hydrocarbons, alcohol, ketones and esters are insoluble, along with the solvent used in the oxidation step.

As above, the catalyst may be in the organic fraction and will be recycled into the reaction medium. It may also be in the fraction containing the carboxylic acids, referred to, in the interests of greater simplicity, as the aqueous phase. The catalyst is recovered according to the usual techniques listed above.

According to the present invention and a first embodiment thereof, the step consisting of hydrolysis by addition of an acid and maintenance at temperature is carried out on the reaction medium before separation of the carboxylic acid or on the medium recovered after separation by settling out or filtration of the crystallized acid.

According to a second embodiment of the invention, the hydrolysis of the esters is carried out by addition of an acid to the separated liquid organic phase, before the recycling into the oxidation reactor, and optionally water.

In these two embodiments, it may be advantageous to separate, prior to the addition of the strong acid, the organic compounds such as the hydrocarbon that has not reacted, the alcohols and ketones formed and all the other products having a boiling point lower than said alcohols and ketones, and also the monocarboxylic solvent, in an advantageous embodiment of the invention.

In these various embodiments, the recovered carboxylic acid can be purified according to the usual techniques described in many documents, for example by crystallization and recrystallization from various solvents such as water, acetic acid or other organic solvents. Purification processes are in particular described in French Patents Nos. 2,749,299 and 2,749,300.

Similarly, if the catalyst is not entirely recycled with the organic phase, and is partly or completely extracted with the aqueous phase, it will be advantageously extracted from the aqueous phase by various techniques, such as liquid/liquid extraction, electrodialysis, or treatment on ion exchange resin, for example.

The process of the invention makes it possible to limit the formation of by-products that are in particular formed by the oxidation of the esters if the latter are not eliminated before the recycling. In addition, the elimination of the esters and the limitation of the formation of by-products make it possible in particular to maintain the activity of the oxidation catalyst and to facilitate the extraction of the diacids formed from the oxidation medium.

Other advantages and details of the invention will become apparent in view of the examples given below, only by way of indication.

EXAMPLES 1-A AND 1-B

Oxidation:

4 g of cobalt tetrahydrate, 357 g of acetic acid, 290 g of cyclohexane and 3.6 g of cyclohexanone (initiator) are placed in a 1.5 l reactor. The mixture is stirred at 105° C. under a pressure of 20 bar and under a continuous stream of gas containing nitrogen and oxygen. After 50 l of oxygen have been consumed, a cyclohexane solution and a solution of acetic acid containing 1.1% by mass of cobalt are injected continuously, the level in the reactor being maintained constant. The reaction mass is recovered in a glass receptacle maintained at 70° C.

The reaction mixture continuously obtained is distilled under vacuum (120-145° C., 0.6 to 0.3 bar). Out of a mass of 2340 g involved in the distillation, a distillation bottom product of 510 g is recovered. This bottom product constitutes "the reaction mixture after distillation of the light products" treated in Example 1-A below.

For Example 1-B, the reaction mixture used is the "reaction mixture after distillation of the light products" above that has undergone further elimination of the cyclohexanol/cyclohexanone (hereinafter referred to as "olone") compounds by azeotropic distillation in the presence of water.

1-A Hydrolysis without Catalyst

The hydrolysis of the reaction mixture after distillation of the light products (18.6 g) is carried out in the presence of $H_2O$ (7.2 g), i.e. a water/ester molar ratio=77.5. The mixture is stirred at 115° C. for 18 h, with continuous elimination of cyclohexanol using a "Dean-Stark" apparatus.

Under these conditions, 20% of the cyclohexyl esters are hydrolysed.

1-B Hydrolysis in the Presence of a Catalyst

The hydrolysis of the reaction mixture after distillation of the light products and azeotropic distillation of the olone (15.3 g) is carried out in the presence of $H_2O$ (12.1 g, including 4.8 g of 2N nitric solution). The mixture is stirred at 127° C. for 18 h, with continuous elimination of cyclohexanol using a "Dean-Stark" apparatus.

Under these conditions 90% of the cyclohexyl esters are hydrolysed.

EXAMPLES 2-A AND 2-B

In these examples, the "reaction mixture leaving the reactor" is obtained as follows:

522 g of cyclohexane, 55 g of tert-butylbenzoic acid and 6 g of cyclohexanone (initiator) are placed in a 1.5 l reactor. Manganese and cobalt are added in respective amounts of 50 and 20 ppm by mass.

The mixture is stirred at 130° C., 20 bar, for 150 min under a continuous stream of gas containing nitrogen and oxygen. After 63 l of oxygen have been consumed, the stream of gas is stopped, the mixture is cooled, and the reactor is depressurized. A mass of 300 g of water is added to the reactor with gentle stirring. The content of the reactor is transferred into a settler. After separation by settling out, two phases are recovered: a lower phase, referred to as aqueous phase, which contains essentially the diacids produced and the catalytic metals, and an upper phase, referred to as organic phase, which contains essentially cyclohexane, tert-butylbenzoic acid, cyclohexanone, cyclohexanol and other by-products of the reaction, including esters.

2-A Hydrolysis with Purolite NRW/160 Resins

The hydrolysis of the reaction mixture leaving the reactor (5.37 g) is carried out in the presence of $H_2O$ (5.14 g) and of a sulphonic resin sold by the company Aldrich under the name Purolite NRW160 (1.01 g). The mixture is stirred at 80° C. for 4 h.

Under these conditions, approximately 30% of the cyclohexyl esters are hydrolysed.

2-B Hydrolysis with Purolite NRW160 Resins

The hydrolysis of the reaction mixture leaving the reactor (5.28 g) is carried out in the presence of $H_2O$ (5.07 g) and of a Purolite NRW160 sulphonic resin (5.03 g). The mixture is stirred at 100° C. for 4 h.

Under these conditions, approximately 70% of the cyclohexyl esters are hydrolysed.

EXAMPLE 3

Hydrolysis in the Presence of $H_2SO_4$

The hydrolysis of a reaction mixture after distillation of the light products corresponding to that used in Example 1-A (2.6 g, including 0.55 g of esters) is carried out in the presence of $H_2O$ and $H_2SO_4$ (1 g of water, including 1% by mass of $H_2SO_4$). The mixture is stirred at 160° C. for 12 h.

Under these conditions, approximately 85% of the cyclohexyl esters are hydrolysed.

EXAMPLE 4

Hydrolysis with Amberlyst A31 Resin

The hydrolysis of a reaction mixture (10 g) corresponding to Example 2A and after distillation of the compounds having a boiling point lower than or equal to that of the acid solvent tBBA is carried out in the presence of 20 ml of Amberlyst A31 resin (sold by the company Rohm and Haas) and of 90 g of $H_2O$. The mixture is heated to 100° C., with continuous elimination of the cyclohexanol formed, using a Dean-Stark apparatus. The mixture is stirred at 100° C. for 4 h.

Under these conditions, approximately 95% of the esters are hydrolysed and the cyclohexanol formed is recovered.

EXAMPLE 5

Hydrolysis in the Presence of $HNO_3$

The hydrolysis of a reaction mixture (1.4 g) equivalent to Example 2A, after distillation of the light products and of the tBBA, is carried out in the presence of $HNO_3$ at 60% in water (10.1 g) and in the presence of a catalyst consisting of a small amount of $Cu(NO_3)_2$, $VO_3NH_4$ and $NaNO_2$.

The mixture is stirred for 1 h at 70° C.

Under these conditions, the esters are completely hydrolysed and the cyclohexanol formed is completely converted to adipic acid.

The invention claimed is:

1. A process for producing carboxylic acids by oxidation of a hydrocarbon with oxygen or a gas containing oxygen with the formation of esters in a reaction medium, in the presence of a monocarboxylic acid-based solvent and of an oxidation catalyst, comprising the steps of hydrolysing the esters formed as byproducts by carrying out a treatment of the reaction medium before extraction of the carboxylic acids or a treatment of the organic phase derived from the reaction medium after extraction of the carboxylic acids formed, wherein said hydrolysis is carried out by addition of a strong acid to the medium to be treated.

2. A process according to claim 1, wherein the medium is maintained at a temperature of greater than 50° C., optionally of between 80° C. and 200° C.

3. A process according to claim 1, wherein the strong acid has a pKa of less than or equal to 2.

4. A process according to claim 3, wherein the strong acid is carried on or attached to an inert material such as a resin.

5. A process according to claim 4, wherein the resin is a sulphonic acid resin.

6. A process according to claim 1, wherein the extraction of the carboxylic acids produced from the reaction medium is carried out by means of separation by settling out.

7. A process according to claim 1, wherein the extraction of the carboxylic acids produced from the reaction medium is obtained by liquid/liquid extraction.

8. A process according to claim 1, wherein the organic phase obtained after extraction of the carboxylic acids and hydrolysis of the esters is recycled at the oxidation step.

9. A process according to claim 1, wherein the organic phase recovered after separation of the diacids formed is subjected to distillation of the compounds having a boiling point less than or equal to that of the alcohol formed during the oxidation step, before the hydrolysis step.

10. A process according to claim 1, wherein the organic phase recovered after separation of the diacids formed is subjected to distillation of the compounds having a boiling point less than or equal to that of the acid solvent used in the oxidation step, before the hydrolysis step.

11. A process according to claim 1, wherein the acids formed during the hydrolysis step are extracted from the medium with a solvent for said acids.

12. A process according to claim 11, wherein the oxidation solvent present in the hydrolysis medium is extracted and purified before recycling at the oxidation step.

13. A process according to claim 11, wherein the acids recovered from the hydrolysis medium are mixed with the diacids extracted from the oxidation medium or in the oxidation medium before extraction of the diacids.

14. A process according to claim 1, wherein the hydrocarbon is a cycloalkane.

15. A process according to claim 14, wherein the cycloalkane is cyclohexane or cyclododecane.

16. A process according to claim 1, wherein the solvent is a monocarboxylic acid having from 1 to 6 carbon atoms, or an acid lipophilic in nature, having from 7 to 20 carbon atoms.

17. A process according to claim 16, wherein the lipophilic acid is hexanoic acid, heptanoic acid, octanoic acid, 2-ethylhexanoic acid, nonanoic acid, decanoic acid, undecanoic acid, dodecanoic acid, stearic acid (octadecanoic acid) and their permethylated derivatives, 2-octadecylsuccinic acid, 3,5-ditert-butylbenzoic acid, 4-tert-butylbenzoic acid, 4-octylbenzoic acid, tert-butyl hydrogen orthophthalate, alkylnaphthenic acid, alkylanthracenic acid, a substituted derivative of phthalic acids, or a fatty diacid.

18. A process according to claim 17, wherein the lipophilic acid is a dimer fatty acid, a naphthenic acid substituted with tert-butyl groups, or an anthracenic acid substituted with tert-butyl groups.

19. A process according to claim 1, wherein the catalyst is a transition metal.

20. A process according to claim 19, wherein the catalyst is based on manganese in combination with a co-catalyst which is cobalt, zirconium, cerium, hafnium or iron.

21. A process according to claim 1, wherein the polycarboxylic acid produced is adipic acid, succinic acid, glutaric acid, dodecanedioic acid or a mixture thereof.

* * * * *

UNITED STATES PATENT AND TRADEMARK OFFICE
CERTIFICATE OF CORRECTION

| | | |
|---|---|---|
| PATENT NO. | : 7,253,312 B2 | Page 1 of 1 |
| APPLICATION NO. | : 10/533212 | |
| DATED | : August 7, 2007 | |
| INVENTOR(S) | : Didier Bonnet et al. | |

It is certified that error appears in the above-identified patent and that said Letters Patent is hereby corrected as shown below:

Title Page
Item (22) PCT Filing Date please change from "Oct. 8, 2003" to --Oct. 28, 2003--.

Signed and Sealed this

Fourth Day of December, 2007

JON W. DUDAS
*Director of the United States Patent and Trademark Office*